United States Patent [19]

An et al.

[11] Patent Number: 6,066,471
[45] Date of Patent: May 23, 2000

[54] PROTEINASE INHIBITOR FOR FOOD PROCESSING

[75] Inventors: Haejung An, Warrenton; David Barnes; Fugen Li, both of Corvallis; Thomas A. Seymour, Warrenton; Michael T. Morrissey, Astoria, all of Oreg.

[73] Assignee: Oregon State University, Corvallis, Oreg.

[21] Appl. No.: 08/975,274

[22] Filed: Nov. 21, 1997

Related U.S. Application Data

[60] Provisional application No. 60/031,817, Nov. 26, 1996.
[51] Int. Cl.7 .......................... C12P 21/06; C07H 17/00; C07K 14/00
[52] U.S. Cl. ...................... 435/69.1; 435/320.1; 435/325; 435/252.3; 530/350; 530/300; 536/23.1
[58] Field of Search .......................... 536/23.1; 435/69.1, 435/320.1, 325, 252.3, 254.2; 530/350, 300, 329, 228

[56] References Cited

PUBLICATIONS

Yamashita, GenBank, Accession No. D86628 "Chum Solmon mRNA . . . ", Nov. 12, 1996.

Li, GenBank, Accession No. U33555 "Oncorhynchus mykiss cystatin cRNA . . . ", Nov. 29, 1995.

Yamashita & Kongagaya, *J. Biochem.* 120(3): 483–487 (1996).

*Primary Examiner*—Karen Cochrane Carlson
*Attorney, Agent, or Firm*—Klarquist Sparkman Campbell Leigh & Whinston, LLP

[57] ABSTRACT

A cDNA encoding the cysteine proteinase inhibitor cystatin has been isolated from trout. The encoded cystatin protein is useful to inhibit cysteine proteinases in food processing, for example in the production of surimi. The full-length cystatin cDNA clone comprises 674 base pairs and encodes a protein of 132 amino acid residues, which is processed to a mature protein of 111 amino acids.

17 Claims, 1 Drawing Sheet

Fig. 1

CAAAGATATCTAACGGGAAAATGATCATGGAATGGAAAATCGTCGTTCCTTTGTTCGCCG 60
                                M  I  M  E  W  K  I  V  V  P  L  F  A  V

TGGCCTTTACGGTGGCGAACGCCGGTTTGATCGGAGGCCCCATGGACGCAAATATGAACG 120
  A  F  T  V  A  N  A  G  L  I  G  G  P  M  D  A  N  M  N  D
        -1  +1                                     10

ACCAAGGAACGAGAGACGCCCTGCAGTTCGCGGTGGTCGAACACAACAAGAAAACAAACG 180
  Q  G  T  R  D  A  L  Q  F  A  V  V  E  H  N  K  K  T  N  D
          20                                30

ACATGTTTGTCAGGCAGGTGGCCAAGGTTGTCAATGCACAGAAGCAGGTGGTATCTGGGA 240
  M  F  V  R  Q  V  A  K  V  V  N  A  Q  K  Q  V  V  S  G  M
          40                              50

TGAAGTACATCTTCACAGTGCAGATGGGCAGGACCCCATGCAGGAAGGGAGGTGTTGAGA 300
  K  Y  I  F  T  V  Q  M  G  R  T  P  C  R  K  G  G  V  E  K
          60                              70

AGGTCTGCTCCGTGCACAAGGACCCACAGATGGCTGTGCCCTACAAGTGCACCTTCGAGG 360
  V  C  S  V  H  K  D  P  Q  M  A  V  P  Y  K  C  T  F  E  V
          80                              90

TGTGGAGCATCCCCTGGATGAGCGATATCCAGATGGTCAAGAACCAGTGTGAAAGTTAAG 420
  W  S  I  P  W  M  S  D  I  Q  M  V  K  N  Q  C  E  S
          100                          110

ACCCAGTGAAGAGAACTTCAATCAATGTCTAGTCTACCCAATAACTACTATTATCTAGTA 480
CTAGTGTTATTTGTTAGTCTCACCAATGCAGTTCAACCTCCTTGTCTAGGATGTATTCAG 540
AGAATCCCACTAATAAAAGATGTTCAAACTTATTGCATGCCCACACTAATATAAGCACTT 600
AATGCAAACATTGCTGTCTTGAGAATGTAGTATTAAAATGATGCAACAGTTAACTA<u>AATA</u> 660
<u>AA</u>TGTTTTGGAACA                                                             674

PROTEINASE INHIBITOR FOR FOOD PROCESSING

PRIORITY CLAIM

This application claims priority to co-pending U.S. provisional patent application serial No. 60/031,817, filed on Nov. 26, 1996, which is incorporated herein by reference.

ACKNOWLEDGMENT OF GOVERNMENT SUPPORT

This research was supported in part by an Oregon Sea Grant with funds from NOAA, Office of Sea Grant, U.S. Dept. of Commerce, under Grant Nos. NA36RG0451 (Project No. R/SF-1) and NIEHS06011. The Government may have certain rights in this invention.

INTRODUCTION

Surimi consumption has increased dramatically since 1980; currently production is at approximately 155 million pounds per year. Surimi is washed minced fish muscle which forms a thermo-irreversible elastic gel upon heating. The gel-forming ability, bland taste, and color of surimi gel have made it possible to use surimi as a main ingredient in seafood analog products such as imitation crab legs, scallops, and shrimp. The strength of surimi gel is critical in making such products, and this is reflected by the commercial pricing of the gel based on its gel strength.

Although Alaskan pollock has been the primary fish species used in surimi production, there has been an effort to utilize other fish species, including Pacific whiting, arrowtooth flounder, and croaker. In the past, these species have been avoided because of their extremely soft texture. Pacific whiting is the most abundant marine resource on the Northwest coast of the U.S. Domestic processing of Pacific whiting increased from 12,000 metric tons (MT) in 1990 to over 200,000 MT by 1994. A large part of the harvest has been used for surimi production because of its relative abundance and low price.

However, production of Pacific whiting surimi presents a significant technical challenge because the myofibrillar components of the flesh are very sensitive to proteolytic degradation. Such degradation interferes with optimal surimi gel formation. Degradation of the muscle proteins peaks at temperatures around 55° C. and, at this temperature, approximately 90% of the myosin molecules in the fish muscle are hydrolyzed within 5 min. Since surimi gel strength is a function of myosin heavy chain molecules (which form a cross-linked network during setting), the rapid degradation of myosin in Pacific whiting muscle causes a serious loss of surimi gel strength (Morrissey et al., 1993).

The proteinase responsible for weakening the gel strength in Pacific whiting surimi has been identified as cathepsin L (Seymour et al., 1994). Cathepsin L is a lysosomal cysteine protease which is highly active on a variety of protein substrates. The purified Pacific whiting cathepsin L is highly active against myofibrillar proteins and is thermostable, having maximum activity at 55° C.

Several proteinase inhibitors have been used to control proteolytic activity in muscle and thus improve the physical properties of surimi gels. (Reppond and Babbitt, 1993) Currently, the most commonly used food-grade inhibitors are beef plasma proteins (BPP), egg white, and potato powder. Despite their gel enhancing activity, these food-grade inhibitors, are of limited use because they have a negative impact on surimi quality. For example, BPP imparts grayish off-colors and results in off-flavors at concentrations above 1% (Akazawa et al., 1993). Similarly, egg white is costly and has an undesirable egg-like odor at levels required for inhibition (Porter et al., 1993). Potato powder does not show any sensory limitations but causes some off-colors (Akazawa et al., 1993). Thus, there is a need for alternative food-grade proteinase inhibitors for use in processing alternative fish species, such as Pacific whiting, for surimi production.

SUMMARY OF THE INVENTION

The present invention is founded on the isolation and cloning of a nucleic acid molecule encoding trout cystatin. Cystatin is a naturally occurring proteinase inhibitor. The trout cystatin cDNA disclosed hereiin includes an open reading frame of 396 base pairs which encodes a 132 amino acid cystatin peptide. The peptide includes a 21 amino acid signal sequence which is likely cleaved in vitro to yield a 111 amino acid mature cystatin peptide.

The trout cDNA sequence can be introduced into host cells, such as yeast, in order to produce large quantities of recombinant cystatin. This recombinant cystatin will be useful to inhibit degradation of fish muscle by native proteinases. In particular, the recombinant cystatin may be added to the meat of fish species such as Pacific whiting to reduce muscle breakdown prior to processing for surimi production.

BRIEF DESCRIPTION OF THE DRAWINGS

FIG. 1 shows the complete nucleotide sequence of the trout cystatin cDNA and the deduced amino acid sequence of the cystatin peptide encoded by this cDNA. The putative signal peptide appears before the amino-terminal glycine, residue +1. The polyadenylation signal is underlined. This sequence is also shown in Seq. I.D. No. 1, together with the deduced amino acid sequence of the encoded peptide. These sequences are also available from GenBank (www.ncbi.nlm.nih.gov) under accession number U33555. The amino acid sequence of the 111 amino acid mature peptide is shown in Seq. I.D. No. 2.

DETAILED DESCRIPTION OF THE INVENTION

1. Cystatins

A number of cystatins have been studied in different species; there is a cystatin superfamily which is divided into three families on the basis of their molecular structures (Barrett et al., 1986). Family 1 cystatins lack disulfide bonds; human cystatins A (Machleidt et al., 1983) and B (Ritonja et al., 1985) and rat cystatins α (Takio et al., 1983) and β (Takio et al. 1984) are typical examples. Family 2 cystatins contain two disulfide bonds as exemplified by human cystatin C (Abrahamson et al., 1987), human cystatin S (Isemura et al., 1986) and chicken cystatin (Colella et al., 1989), mouse cystatin (Solem et al., 1990) and rat cystatin (Cole et al., 1989). Both families are also characterized by their molecular weights that range from 10,000 to 20,000 Da. Family 3 cystatins comprise kininogen segments (Abe et al., 1987). The various cystatins in these three families are well characterized biochemically.

Although the amino acid sequence of chum salmon cystatin is known (Koide and Noso, 1994), little additional information is known about fish cystatins at the molecular level. It is known that cystatin is involved in the regulation of various fish proteinases in vivo. Salmon goes through extensive hydrolysis of muscle proteins during spawning migration, resulting in softening of fish flesh. The activity of the proteinase cathepsin L has been shown to be involved in hydrolysis of muscle proteins and is known to be substantially increased in salmon flesh during spawning migration (Yamashita and Konagaya, 1990). Cystatin activities in white muscle, serum, and other tissues of salmon in spawning migration are lower than those in feeding migration, and this lowered cystatin activity has been proposed to cause the increased level of cathepsin proteinase.

2. Cloning of Trout Cystatin cDNA: Materials and Methods

A. Materials

Materials and reagents were purchased from the following sources:

TRI REAGENT: Molecular Research Center, Inc, (Cincinnati, Ohio).

Reverse transcription system kit, Lambda gt 11 system, subcloning plasmid pGEM3Z and Lambda DNA packaging system: Promega (Madison, Wis.).

PCR reagent kit: Perkin-Elmer Cetus (Norwalk, Conn.).

Geneclean kit: Bio 101 (La Jolla, Calif.).

cDNA synthesis kit: Pharmacia Biotech (Uppsala, Sweden).

BioMag mRNA purification kit: PerSeptive Diagnostics Inc. (Cambridge, Mass.).

Random primed DNA labeling kit: Boehringer Mannheim Biochemica (Indianapolis, Ind.).

Temperature cycler: Ericomp Inc.(San Diego, Calif.).

$\alpha$-$^{32}$p dATP and $\alpha$-$^{32}$p dCTP: Du Pont Co. (Wilmington, Del.)

B. Generation of Trout Cystatin Probe by RT-PCR

Initial experiments to clone the trout cystatin cDNA using a mammalian cystatin cDNA as a probe were unsuccessful. This is likely attributable to the fact that the homologies between various mammalian cystatin cDNAs are quite low (Barrett, 1987; Barrett, et al., 1986; Colella et al., 1989). Accordingly, an alternative approach was adopted in which degenerate PCR primers, derived from stretches of amino acid sequences which are conserved between various cystatins, were used to amplify a sequence from trout RNA by reverse transcriptase PCR (RT-PCR). This amplified sequence was then used as a probe to probe a cDNA library.

Degenerate deoxyoligonucleotide primers for use in RT-PCR were synthesized with an automated synthesizer. The primers were based on the corresponding amino acid sequences of highly conserved regions in family 2 cystatins. The primers used were:

Primer 1:

AA(C/T)GCCCA(A/G)AA(A/G)CAGGT(A/G/C/T)GTGTC(A/G/C/T)GG (128 combinations)   (Seq. I.D. No. 3)

Primer 2:

CATCCA(A/G/C/T)GG(A/G/T)AT(A/G)CTCCA(A/G/C/T)AC(C/T)AC(A/G)AA (384 combinations)   (Seq. I.D. No. 4)

Total RNA was extracted from livers of rainbow trout by the TRI REAGENT methods (Chomezynski 1993). Total RNA was used to make first strand cDNA which was boiled at 100° C. for 5 min. and stored at −20° C. for reverse transcription PCR (RT-PCR). PCR with the thermostable DNA polymerase of *Thermus aquaticus* (Taq), was performed as described previously (Saiki et al., 1988) except that degenerate oligonucleotide primers were used at a final concentration of 1 uM to 4 uM, and Taq polymerase concentrations per 50 ul reaction/MgCl$_2$ were 2.0 unit/1.5 mM and 1.25 unit/2.5 mM. The first three amplification cycles were performed at an annealing temperature of 37° C., and subsequent 35 cycles were carried out using a denaturation temperature of 94° C. for 30 seconds, an annealing temperature of 48° C. for 1 minute and an extension temperature of 70° C. for 1 minute. In the final cycle the extension was performed for 5 minutes at 70° C. The predicted size of the PCR product was 168 bp.

PCR products were analyzed by 3% Nusieve agarose (FMC BioProducts, Rockland, Me.) and 1% agarose gel electrophoresis (Sambrook et al. 1989). A PCR product with the predicted size was isolated and purified with a Geneclean kit according to protocols provided by Bio 101. Direct sequencing of the PCR product confirmed that the amplified fragment was likely to be part of the trout cystatin cDNA; this fragment was subsequently used to probe the trout liver cDNA library to clone the full length cystatin cDNA, as described below.

C. Construction of Rainbow Trout Liver cDNA Library

Total RNA was extracted from liver of rainbow trout by the TRI-REAGENT method (Chomezynski 1993). Poly(A$^+$) RNA was purified using a BioMag mRNA purification kit. After the synthesis of single-stranded cDNA by reverse transcriptase with total poly(A$^+$) RNA as a template, double-stranded cDNA was synthesized essentially according to the method of Gubler and Hoffman (1983) using *E. coli* polymerase I. Flush ends of the cDNA were generated with T4 DNA polymerase and ligated with EcoR I/Not I adaptors, and inserted into the phage vector $\lambda$gt 11. The DNA was then packaged into bacteriophage particles using the lambda packaging system (Promega), and grown on *E. coli* strain LE392.

D. Library Screening

Recombinant plaques were transferred onto nitrocellulose (Schleicher & Schuell, Keene, N.H.). The filters were dried in a vacuum oven at 80° C. for 2 hours and prehybridized with the solution containing 6×SSC, 5×Denhardt's reagent, 0.5% SDS, 50% formamide and 100 ug/ml denatured sonicated calf thymus DNA at 42° C. for 4 hours. After the prehybridization, the filters were hybridized with the partial cystatin cDNA probe described above, labeled using radioactive nucleotides in the same solution used for the prehybridization at 42° C. for 20 hours. The filters were finally washed in 0.25×SSC, 0.1% SDS at 65° C. and exposed to hyperfilm with an intensifying screen at −80° C. The positive plaques selected on the first screening were re-screened under the same conditions.

E. DNA Sequencing Analysis

DNA from positive recombinant phages was isolated according to the method described by Sambrook et al., (1989). All DNA from positive recombinant was cut with EcoRI to check the size of the inserts. Two primers from $\lambda$gt11 arms were used for DNA sequencing to identify the correct clone. Thereafter, the selected clone was digested with EcoRI and the insert was subcloned into the EcoRI site of pGEM3Z (Promega) and re-sequenced.

F. Northern Blotting

Total RNA was extracted from the different tissues of rainbow trout. 10 $\mu$g of total RNA from each sample was denatured and electrophoresed in a formaldehyde-containing agarose gel. After electrophoresis, the RNA was transferred to a nylon membrane (INC Biomedical Inc., Ohio) and hybridized with labeled cystatin cDNA at 42° C. in a solution containing 5×Denhardts, 5×SSC, 50 mM sodium phosphate(pH 6.5), 0.1% SDS, 50% formamide, and 100 $\mu$g/ml heat-denatured sonicated calf thymus DNA. The filter was washed with 1×SSC containing 0.1% SDS at room temperature for 30 min, with 0.25×SSC containing 0.1% SDS at room temperature for 15 min and then exposed to hyperfilm at −80° C.

G. Southern Blotting

Trout genomic DNA was isolated from liver tissue according to the method of Sambrook et al., (1989). About 20 μg of the DNA was digested with various restriction enzymes, electrophoresed on 1% agarose gel, denatured and transferred to nitrocellulose membrane and hybridized with labeled cystatin cDNA at 42° C. The filters were washed with 0.25×SSC containing 0.1% SDS at 65° C. and then exposed to hyperfilm at −80° C.

3. Cloning of Trout Cystatin cDNA: Results

From 1.2×10$^4$ independent cDNA clones in the trout liver λgt11 cDNA library, 4 clones were identified which hybridized with the $^{32}$P-labeled partial trout cystatin cDNA probe. These four positive clones were designed as cst1, cst2, cst3 and cst4; all four were sequenced initially with two primers from λgt11 arms. Clone cst2 was selected for further study, subcloned into the plasmid vector pGEM3Z and resequenced. FIG. 1 shows the complete nucleotide sequence of the trout cDNA insert in cst2 and the amino acid sequence of the encoded peptide. The cDNA sequence is 674 bp in length; it contains a 3' AATAAA polyadenylation signal, but lacks a poly(A) tail. The encoded peptide is 132 amino acids long.

4. Characterization of Clone Cst2 as Trout Cystatin, A Member of Cystatin Family 2

As noted above, the cystatin superfamily of proteins consists of three subgroups, referred to as family 1, 2 and 3 cystatins. The mature trout cystatin consists of 111 amino acid residues and contains 4 cysteine residues which should form two disulfide linkages. A comparison of the amino acid sequence of trout cystatin to other previously described family 2 cystatins was made. The trout cystatin shows good homology with other family 2 cystatins, particularly in those stretches of sequence representing consensus sequences of reactive sites: Gly(4), Gln-X-Val-Gly(48–52), and Ile(Val)-Pro-Trp(96–98). Based on the X-ray crystallographic study of chicken cystatin, these consensus amino acid sequences were considered to be essential for the interaction between chicken cystatin and papain (Machleidt et al., 1993). Since trout cystatin is conserved in those reactive sites, it is suggested that trout cystatin belongs to cystatin family 2.

The precursor trout cystatin contains a putative hydrophobic signal peptide of 21 amino acid residues and a mature sequence of 111 amino acid residues. The cleavage site for the signal peptide is proposed to be between the Ala residue at position −1 and the Gly residue at position +1 (FIG. 1). The presence of a signal sequence in trout cystatin suggests that this protein exists predominantly in the extracellular space, as do most members of cystatin family 2.

The percentage of amino acid sequence identities between trout cystatin and other cystatins are as follows: 96% with salmon cystatin (Koide and Noso, 1994), 43% with chicken cystatin (Colella et al., 1989), and 35% with mouse (Solem et al, 1990), rat (Cole et al., 1989) and human (Abrahamson et al., 1987) cystatins.

5. Expression of Trout Cystatin Gene in Various Tissues

The trout cystatin cDNA was used as a hybridization probe on Northern blots to evaluate the expression of trout cystatin mRNA. Cystatin mRNA was present in almost all trout tissues studied but showed variation in its steady-state level (data not shown). The highest concentrations of cystatin mRNA were found in brain and eggs developed for 25 days. Lower levels of cystatin mRNA were detected in liver and muscle. The size of the detected trout cystatin mRNA was constant in all tissues at about 900 bp.

6. Determination of Trout Cystatin Genomic Gene Copy Number

To determine the copy number of the trout cystatin gene in the trout genome, genomic DNA of rainbow trout was digested with EcoRI and HindIII and Southern blotted onto a nitrocellulose membrane. The $^{32}$P-labeled trout cystatin cDNA was used as a hybridization probe. The results showed one primary hybridizing band, although faint additional bands were detectable. This suggests that the copy number of the trout cystatin gene is probably one per haploid genome.

Having herein presented the cDNA sequence for trout cystatin, this invention enables the expression of recombinant trout cystatin in host cells, such as yeast. Bulk production of recombinant cystatin will allow the large scale use of the protein as a proteinase inhibitor. This is expected to be of particular value in the fish processing industry. The following examples of illustrative of various applications which are made possible for the first time by this invention.

EXAMPLE ONE

Preferred Method of Making the Trout Cystatin cDNA

Having herein provided the sequence of the trout cystatin cDNA, one skilled in the art will recognize that the full length cDNA clone can now readily be obtained by standard methods, without resort to the library screening procedure described above. Such methods include, for example, the polymerase chain reaction (PCR) by which means DNA sequences can be amplified. Methods and conditions for PCR amplification of DNA are described in Innis et al. (1990) and Sambrook et al. (1989).

The selection of PCR primers for amplification of the trout cystatin cDNA will be made according to the portions of the cDNA which are desired to be amplified. Primers may be chosen to amplify small fragments of the cDNA or the entire cDNA molecule. Variations in amplification conditions may be required to accommodate primers of differing lengths; such considerations are well known in the art and are discussed in Innis et al. (1990). By way of example only, the entire open reading frame of the trout cystatin cDNA may be amplified using the following primers.

Primer 1: 5' ATGATCATGGAATGGAAAATC
GTC 3'                                      (Seq. I.D. No. 5)

Primer 2: 5' ACTTTCACACTGGTTCTTGAC
CAT 3'                                      (Seq. I.D. No. 6)

Template DNA for PCR amplification to produce the trout cystatin cDNA can be extracted from a trout cDNA library produced as described above.

Alternatively, the whole trout cystatin cDNA may be obtained by PCR amplification of reverse transcribed RNA (RT-PCR) essentially as described above, but using primers selected to amplify the entire cDNA.

Standard methods for the purification and cloning of PCR products are well known in the art and are described by Innis et al. (1990) and Sambrook et al. (1989).

EXAMPLE TWO

Isolation of Cystatin Genes from Other Fish Species

The provision herein of the trout cystatin cDNA sequence enables the cloning of cystatin cDNAs from other fish species. The methods described above in Example One for obtaining the trout cystatin cDNA may be applied to cDNA libraries made from, or RNA extracted from, tissues of other fish species, such as Pacific whiting and salmon, in order to obtain cystatin cDNAs from such species. This invention encompasses cystatin cDNA sequences from other fish species.

EXAMPLE THREE

Nucleotide Sequence Variants of Trout Cystatin cDNA and Amino Acid Sequence Variants of Trout Cystatin Protein FIG. 1 show the nucleotide sequence of the trout cystatin cDNA and the amino acid sequence of the trout cystatin protein which is encoded by this cDNAs. For the purposes of the present invention, the functional characteristic of the trout cystatin protein is its ability to inhibit the activity of Pacific whiting cathepsin L. This activity can be measured using the assay described in Example Six below.

Having presented the nucleotide sequence of the trout cystatin cDNA and the amino acid sequence of the encoded protein, this invention now also facilitates the creation of DNA molecules, and thereby proteins, which are derived from those disclosed but which vary in their precise nucleotide or amino acid sequence from those disclosed. Such variants may be obtained through a combination of standard molecular biology laboratory techniques and the nucleotide sequence information disclosed by this invention.

Variant DNA molecules include those created by standard DNA mutagenesis techniques, for example, M13 primer mutagenesis. Details of these techniques are provided in Sambrook et al. (1989), Ch. 15. By the use of such techniques, variants may be created which differ in minor ways from those disclosed. DNA molecules and nucleotide sequences which are derivatives of those specifically disclosed herein and which differ from those disclosed by the deletion, addition or substitution of nucleotides while still encoding a protein which possesses the functional characteristic of the trout cystatin protein are comprehended by this invention. Also within the scope of this invention are small DNA molecules which are derived from the disclosed cDNA sequence. Such small DNA molecules include oligonucleotides suitable for use as hybridization probes or polymerase chain reaction (PCR) primers. As such, these small DNA molecules will comprise at least a segment of the trout cystatin cDNA molecule and, for the purposes of PCR, will comprise at least 10–15 consecutive nucleotides of the trout cystatin cDNA. As one of skill in the art will appreciate, the specificity of PCR amplification may be enhanced by, among other things, increasing the length of the primers used. Thus, nucleic acid molecule which comprise 20, 30, 40 or 50 consecutive nucleotides of the trout cystatin cDNA sequence will provide increasing specificity. DNA molecules and nucleotide sequences which are derived from the disclosed DNA molecules as described above may also be defined as DNA sequences which hybridize under stringent conditions to the DNA sequences disclosed, or fragments thereof.

Hybridization conditions resulting in particular degrees of stringency will vary depending upon the nature of the hybridization method of choice and the composition and length of the hybridizing DNA used. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al. (1989), chapters 9 and 11, herein incorporated by reference. By way of illustration only, a hybridization experiment may be performed by hybridization of a DNA molecule (for example, a probe consisting of part of the trout cystatin cDNA) to a target DNA molecule (for example, a cystatin cDNA from another fish species) which has been electrophoresed in an agarose gel and transferred to a nitrocellulose membrane by Southern blotting, a technique well known in the art and described in Sambrook et al. (1989). Hybridization with the target probe labeled with [$^{32}P$]-dCTP is generally carried out in a solution of high ionic strength such as 6×SSC at a temperature that is 20–25° C. below the melting temperature, $T_m$, described below. For such Southern hybridization experiments where the target DNA molecule on the Southern blot contains 10 ng of DNA or more, hybridization is typically carried out for 6–8 hours using 1–2 ng/ml radiolabeled probe (of specific activity equal to $10^9$ CPM/$\mu$g or greater). Following hybridization, the nitrocellulose filter is washed to remove background hybridization. The washing conditions should be as stringent as possible to remove background hybridization but to retain a specific hybridization signal. The term $T_m$ represents the temperature above which, under the prevailing ionic conditions, the radiolabeled probe molecule will not hybridize to its target DNA molecule. The $T_m$ of such a hybrid molecule may be estimated from the following equation (Bolton and McCarthy, 1962):

$$T_m = 81.5° C. - 16.6(\log_{10}[Na^+]) + 0.41(\% \; G + C) - 0.63(\% \; formamide) - (600/l)$$

Where l=the length of the hybrid in base pairs. This equation is valid for concentrations of $Na^+$ in the range of 0.01 M to 0.4 M, and it is less accurate for calculations of $T_m$ in solutions of higher [$Na^+$]. The equation is also primarily valid for DNAs whose G+C. content is in the range of 30% to 75%, and it applies to hybrids greater than 100 nucleotides in length (the behavior of oligonucleotide probes is described in detail in Ch. 11 of Sambrook et al., 1989).

Thus, by way of example, for a 150 base pair DNA probe derived from the open reading frame of the trout cystatin cDNA (with a hypothetical % GC=45%), a calculation of hybridization conditions required to give particular stringencies may be made as follows:

For this example, it is assumed that the filter will be washed in 0.3×SSC solution following hybridization, thereby

[$Na^+$]=0.045M

% GC=45%

Formamide concentration=0 l=150 base pairs $T_m$=81.5–16($\log_{10}$[$Na^+$])+(0.41×45)–(600)/(150)

and so $T_m$=74.4° C.

The $T_m$ of double-stranded DNA decreases by 1–1.5° C. with every 1% decrease in homology (Bonner et al., 1973). Therefore, for this given example, washing the filter in 0.3×SSC at 59.4–64.4° C. will produce a stringency of hybridization equivalent to 90%; that is, DNA molecules with more than 10% sequence variation relative to the target cDNA will not hybridize. Alternatively, washing the hybridized filter in 0.3×SSC at a temperature of 65.4–68.4° C. will yield a hybridization stringency of 94%; that is, DNA molecules with more than 6% sequence variation relative to the target cDNA molecule will not hybridize. The above example is given entirely by way of theoretical illustration.

One skilled in the art will appreciate that other hybridization techniques may be utilized and that variations in experimental conditions will necessitate alternative calculations for stringency.

In preferred embodiments of the present invention, stringent conditions may be defined as those under which DNA molecules with more than 25% sequence variation (also termed "mismatch") will not hybridize. In a more preferred embodiment, stringent conditions are those under which DNA molecules with more than 15% mismatch will not hybridize, and more preferably still, stringent conditions are those under which DNA sequences with more than 10% mismatch will not hybridize. In a most preferred embodiment, stringent conditions are those under which DNA sequences with more than 6% mismatch will not hybridize.

The degeneracy of the genetic code further widens the scope of the present invention as it enables major variations in the nucleotide sequence of a DNA molecule while maintaining the amino acid sequence of the encoded protein. For example, the thirteenth amino acid residue of trout cystatin is alanine. This is encoded in the cystatin cDNA by the nucleotide codon triplet GCC. Because of the degeneracy of the genetic code, three other nucleotide codon triplets—GCT, GCG and GCA—also code for alanine. Thus, the nucleotide sequence of the cystatin cDNA could be changed at this position to any of these three codons without affecting the amino acid composition of the encoded protein or the characteristics of the protein. The genetic code and variations in nucleotide codons for particular amino acids is presented in Tables 1 and 2. Based upon the degeneracy of the genetic code, variant DNA molecules may be derived from the trout cystatin cDNA molecule disclosed herein using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are herein also comprehended by this invention.

TABLE 1

The Genetic Code

| First Position (5' end) | Second Position | | | | Third Position (3' end) |
|---|---|---|---|---|---|
| | T | C | A | G | |
| T | Phe | Ser | Tyr | Cys | T |
| | Phe | Ser | Tyr | Cys | C |
| | Leu | Ser | Stop (och) | Stop | A |
| | Leu | Ser | Stop (amb) | Trp | G |
| C | Leu | Pro | His | Arg | T |
| | Leu | Pro | His | Arg | C |
| | Leu | Pro | Gln | Arg | A |
| | Leu | Pro | Gln | Arg | G |
| A | Ile | Thr | Asn | Ser | T |
| | Ile | Thr | Asn | Ser | C |
| | Ile | Thr | Lys | Arg | A |
| | Met | Thr | Lys | Arg | G |
| G | Val | Ala | Asp | Gly | T |
| | Val | Ala | Asp | Gly | C |
| | Val | Ala | Glu | Gly | A |
| | Val (Met) | Ala | Glu | Gly | G |

"Stop (och)" stands for the ochre termination triplet, and "Stop (amb)" for the amber. ATG is the most common initiator codon; GTG usually codes for valine, but it can also code for methionine to initiate an mRNA chain.

TABLE 2

The Degeneracy of the Genetic Code

| Number of Synonymous Codons | Amino Acid | Total Number of Codons |
|---|---|---|
| 6 | Leu, Ser, Arg | 18 |
| 4 | Gly, Pro, Ala, Val, Thr | 20 |
| 3 | Ile | 3 |
| 2 | Phe, Tyr, Cys, His, Gln, Glu, Asn, Asp, Lys | 18 |
| 1 | Met, Trp | 2 |
| Total number of codons for amino acids | | 61 |
| Number of codons for termination | | 3 |
| Total number of codons in genetic code | | 64 |

One skilled in the art will recognize that the DNA mutagenesis techniques described above may be used not only to produce variant DNA molecules, but will also facilitate the production of proteins which differ in certain structural aspects from the trout cystatin protein, yet which proteins are clearly derivative of this protein and which maintain the essential functional characteristic of the trout cystatin protein. Newly derived proteins may also be selected in order to obtain variations on the characteristic of the trout cystatin protein, as will be more fully described below. Such derivatives include those with variations in amino acid sequence including minor deletions, additions and substitutions.

While the site for introducing an amino acid sequence variation is predetermined, the mutation per se need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

Amino acid substitutions are typically of single residues; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. Obviously, the mutations that are made in the DNA encoding the protein must not place the sequence out of reading frame and preferably will not create complementary regions that could produce secondary mRNA structure.

Substitutional variants are those in which at least one residue in the amino acid sequence has been removed and a different residue inserted in its place. Such substitutions generally are made in accordance with the following Table 4 when it is desired to finely modulate the characteristics of the protein. Table 3 shows amino acids which may be substituted for an original amino acid in a protein and which are regarded as conservative substitutions.

TABLE 3

| Original Residue | Conservative Substitutions |
|---|---|
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile, val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in protein function are made by selecting substitutions that are less conservative than those in Table 3, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The effects of these amino acid substitutions or deletions or additions may be assessed for derivatives of the trout cystatin protein by analyzing the ability of the derivative proteins to inhibit Pacific whiting cathepsin L.

In one aspect, derivative forms of the trout cystatin may be produced which retain cystatin activity and which have stretches of amino acid sequence that are identical to the trout cystatin sequence shown in Seq. I.D. No. 2. In one embodiment, such cystatin proteins include at least 7 consecutive amino acids of the trout sequence shown in Seq. I.D. No. 2. In another embodiment, such cystatin proteins include at least 10 consecutive amino acids of the trout sequence shown in Seq. I.D. No. 2.

EXAMPLE FOUR

Production of Recombinant Trout Cystatin in Heterologous Systems

Many different expression systems are available for expressing cloned cDNAs. Examples of prokaryotic and eukaryotic expression systems that are routinely used in laboratories are described in Chapters 16–17 of Sambrook et al. (1989), which are herein incorporated by reference. In general, the expression of the trout cystatin cDNA disclosed herein, derivatives thereof and other fish cystatins may be achieved by introducing the nucleic acid molecule encoding the protein into a recombinant expression vector. Expression vectors suitable for use in bacterial and yeast cells are well known in the art. Typically, the nucleic acid sequence that is to be expressed is cloned into the expression vector in operable linkage to a promoter sequence that drives high level expression of downstream sequences. Such promoter sequences may be constitutive or inducible. Once the nucleic acid molecule has been introduced into the expression vector, the resultant construct is then introduced into a suitable host cell (e.g., *Pichia pastoris, Escherichia coli*) using standard transformation techniques.

Because the purified trout cystatin protein will be used to treat harvested fish, it is anticipated that production of the protein in yeast cells will be preferred (from both regulatory and consumer acceptance viewpoints).

By way of example only, high level expression of the trout cystatin protein may be achieved by cloning and expressing the cDNA in yeast cells using the pYES2 yeast expression vector (Invitrogen, San Diego, Calif.). Initial experiments (data not shown) in which trout cystatin was synthesized in yeast cells by placing the cloned cDNA under control of the GAL1 inducible promoter of pYES2 showed that the induced cystatin mRNA level in yeast cells was 100 to 1000-fold that found in trout liver.

The recombinant trout cystatin may be supplied in the harvested yeast cells (for subsequent processing). Alternatively, a genetic construct may be produced to direct secretion of the recombinant cystatin from the yeast cells into the medium. This approach will facilitate the purification of the cystatin protein, if this is necessary. Secretion of the recombinant cystatin from the yeast cells may be achieved by placing a yeast signal sequence adjacent to the trout cystatin coding region. A number of yeast signal sequences have been characterized, including the signal sequence for yeast invertase. This sequence has been successfully used to direct the secretion of heterologous proteins from yeast cells, including such proteins as human interferon (Chang et al., 1986), human lactoferrin (Liang and Richardson, 1993) and prochymosin (Smith et al., 1985).

EXAMPLE FIVE

Purification of Recombinant Cystatin

The purification of recombinant trout cystatin will be facilitated by secretion of the protein from the yeast cells. By way of example, recombinant cystatin may be purified from the yeast growth medium by the following method.

After removal of the yeast cells by centrifugation, the yeast culture broth is filtered to remove any remaining particulate matter filter paper and then diafiltered against 20 mM Tris-HCl/1 mM EDTA (pH 8.0) in a tangential flow filtration system with a pellicon mini-cassette filter (PLGC membrane with 5,000 MW cutoff) (Millopore Corp., Bedford, Mass.) at 4° C. The retentate is diluted with 50 mM ammonium bicarbonate (pH 8.0) and then passed through Whatman No. 1 filter paper to remove any remaining cell debris. The preparation is then chromatographed on a Mono-Q ion-exchange column (Pharmacia LKB Biotechnology) equilibrated with 50 mM ammonium bicarbonate (pH 8.0). Elution is achieved by stepwise increase of ammonium bicarbonate concentration to 50 mM, 100 mM, 500 mM and 1000 mM at pH 8.0. All fraction are assayed for papain inhibition activity as described below. The active fractions may be further separated by gel filtration on a Superdex 75 column (Pharmacia LKB Biotechnology)in 150 mM ammonium bicarbonate (pH 8.0).

EXAMPLE SIX

Cystatin Activity Assay

The inhibitory activity of expressed cystatin may be measured by the method of Izquierdo-Pulido et al. (1994) against papain, as well as against purified Pacific whiting cathepsin L as described by Seymour et al. (1994). For example, to determine activity against papain, α-N-benzoyl-DL-arginine-2-naphthylamide (BANA) is used as a synthetic substrate (Barrett, 1972). Solutions containing equal volume of papain (0.045 mg/mL) and cystatin are added to 100 mM phosphate buffer (pH 6.0) containing 1.33 mM EDTA and 2.7 mM cysteine. The mixture is preincubated for 5 min at 40° C., and 10 μL of 40 mg/mL BANA is added to start the reaction. The reaction mixture is then incubated at 40° C. for 10 min. A color reagent (0.1 mM Fast Garnet GBC base, 0.2 mM sodium nitrite, 2% Brij 35, and 5 mM mersalyl acid) is then added to terminate the reaction, and the mixture is allowed to react for 10 min. for color development. The resultant solution is centrifuged at 8,000 g for 3 min, and cystatin activity is assessed based on the residual activity of papain measured by absorbance at 520 nm. Standards and blanks are prepared by replacing the enzyme with β-naphthylamide and water, respectively.

EXAMPLE SEVEN

Use of Recombinant Trout Cystatin in Surimi Production

Commercially produced surimi from Pacific whiting harvested off the Oregon coast within 24 hr of capture may be used for determining the activity of batches of recombinant cystatin. In commercial surimi production, Pacific whiting muscle is ground, and the resulting mince is washed, dewatered and refined to remove impurities. Surimi is prepared from this material by mixing the mince with cryoprotectants, 4.0% sucrose, 4.0% sorbitol and 0.3% sodium phosphate (Brifisol 512). Testing of the efficacy of recombinant cystatin is determined by adding to this mixture recombinant cystatin, BPP (positive control), or casein (negative control) at temperatures below 10° C. The prepared surimi is then subjected to gel strength measurement, by one of two methods. The standard method for measuring gel strength in surimi gels is the torsion test described by Lanier et al. (1991) and used by the National Fisheries Institute. Alternatively, a quick punch test may be used.

This latter method, developed by T. A. Seymour and M. Y. Peters at the O. S. U. Seafood Laboratory in Astoria, Oreg., may be preferred because it allows processing of a large number of samples per day. It is performed essentially as follows. Frozen surimi, partially thawed and chopped into small pieces, is placed in a porcelain mortar. Surimi paste is prepared with 2% salt and additives, and the moisture is adjusted to 78% with water at 4° C. Mixing is carried out on ice for 7–10 min with a pestle until a uniform paste is formed. The surimi paste is then put into a 8"×10" vacuum bag and vacuum sealed. The paste is squeezed into a 60 ml syringe and pressed into wells of 24-well cell culture plates with two holes on the bottom to release air. Both wells and lids are sprayed with Pam cooking spray. The plates are then sealed in a vacuum bag and heated for 15 min at 90° C. for heat-setting of the gel, followed by cooling in an ice-water bath for 15 min. For measurement of gel strength, samples are set out at room temperature (~21° C.) for 1.5 hrs.

Breaking strength (g) and deformation (cm) are measured with the Sintech (MTS SINTECH, Inc., Research Triangle Park, N.C.) punch test using a 5 mm diameter round end plunger. Samples are measured with the plunger in the center of the cell plate wells. Gel strength is determined by multiplying the breaking strength (g) and deformation (cm) (Lanier, 1992). Samples with a flat line and a breaking strength under 100 g, and a deformation above 1.0 cm are considered to have a gel strength of zero.

EXAMPLE EIGHT

Use of Cystatin for Food Processing

In addition to use in surimi production as discussed above, recombinant cystatin is particularly well suited for use in food processing in general. This is because while cystatin will not inhibit most of the proteinases in the human digestive system (since they are not cysteine proteinases), cysteine proteinases are prevalent in many food products and must be removed or deactivated during processing.

As noted above, cystatin is highly specific for cysteine proteinases, which have a sulfhydryl group in the active site (Anastasi et al., 1983; Abrahamson et al., 1986; Barrett et al., 1986). In contrast, most important digestive enzymes are either serine proteinases (having a hydroxyl group in the active site) or aspartic proteinases (having a carboxyl group in the active site). For example, trypsin, chymotrypsin, and pancreatic elastase are serine proteinases while pepsin is an aspartic proteinase (Barrett and McDonald, 1980, and the references cited therein).

Most proteinases common in muscle (calcium-actived neutral proteinase and cathepsins) or plant systems (papain, bromelain, ficin, etc) are cysteine proteinases. In particular, the plant cysteine proteinases are widely used for food processing, including meat tenderization, preparation of sausage casing, and chillproofing beer. After proteinase treatment, the proteinases are removed by membrane filtration or inactivated by heat. Heat inactivation may be economically feasible, but an extremely high temperature is required in order to inactivate cysteine proteinases due to their thermostability (Yamamoto, 1975). Such high temperature processing may significantly alter the textural property or flavor of the food. In the case of sausage casing preparation, membranes are boiled in order to inactivate the proteinases used in the processing, thus modifying the membrane properties.

Accordingly, the present invention also encompasses the use of cystatin to inactivate proteinases either endogenous in food materials or added during food processing. The use of cystatin provides significant advantages over the existing proteinase removal technologies of harsh heat treatment or expensive membrane filtration. In addition, cystatin used in this manner will be safe for human consumption since it will not interfere with the activity of proteinases present in the human digestive tract. Thus, one aspect of the invention is the use of recombinant cystatin in general food processing.

REFERENCES

Abe, K., Emori, Y., Kondo, H., Suzuki, K. and Arai, S. 1987. Molecular cloning of a cysteine proteinase inhibitor of rice (Oryzacystatin). J. Biol. Chem. 262: 16793–16797.

Abrahamson, M., Grubb, A., Olafsson, I. and Lundwall, A. 1987. Molecular cloning and sequence analysis of cDNA coding for the precursor of the human cysteine proteinase inhibitor cystatin C. FEBS Lett. 216: 229–233.

Abrahamson, M., Barrett, A. J., Salvesen, G., Grubb, A. 1986. Purification, molecular cloning, and sequencing of salivary cystatis SA-1. J. Biol. Chem. 261: 11282–11289.

Akazawa, H., Miyauchi, Y., Sakurada, K., Wasson, D. H., and Reppond, K. D. 1993. Evaluation of protease inhibitors in Pacific whiting surimi. J. Aquat. Food Prod. Technol. 2(3): 79–95.

Anastasi, A., Brown, M. A., Kembhavi, A. A., Nicklin, M. J. H., Savers, C. A., Sunter, D., and Barrett, A. J. 1983. Cystatin, a protein inhibitor of cysteine proteinases. Biochem. J. 211: 129–138.

Barrett, A. J., 1987. The cystatins: a new class of peptidase inhibitors. TIBS 12: 193–196.

Barrett, A. J., Rawling, N. D., Davies, M. E., Machleidt, W., Salvesen, G., and Turk, V. 1986. Chap 18. Cysteine proteinase inhibitors of the cystatin superfamily. In "Proteinase Inhibitors", Barrett, A. J. and Salvesen, G. (Eds.) p. 515–569. Elsevier Sci. Pub. Amsterdam.

Barrett, A. J. 1972. A new assay for cathepsin B1 and other thiol proteinases. Anal. Biochem. 47: 280–293.

Bolton and McCarthy 1962. Proc. Natl. Acad. Sci. USA 48:1390.

Bonner et al. 1973. J. Mol. Biol. 81:123.

Chang, C. N., Matteucci, M., Jeanne Perry, L., Wulf, J. J., Chen, C. Y. and Hitzeman, R. A., 1986. *Saccharomyces cerevisiae* secretes and correctly processes human interferon hybrid protein containing yeast invertase signal peptides. Mol. and Cell. Biol. 6:1812–1819.

Cole, T., Dickson, P. W., Esnard, F., Averill, S., Risbridger, G. P., Gauthier, F. and Schreiber, G. 1989. The cDNA structure and expression analysis of the genes for the cysteine proteinase inhibitor cystatin C and $\beta_2$-microglobulin in rat brain. Eur. J. Biochem. 186: 35–42.

Colella, R., Sakaguchi, Y., Nagase, H. and Bird, John W. C. 1989. Chicken egg white cystatin-molecular cloning, nucleotide sequence, and tissue distribution. J. Biol. Chem. 264: 17164–17169.

Gubler, U. and Hoffman, B. J. 1983. A simple and very efficient method for generating cDNA libraries. Gene 25:263–269.

Innis, M. A., Gelfand, D. H., Sminsk, J. J., White, T. J. 1990. PCR protocols, A guide to methods and applications, Academic Press, Inc., San Diego.

Isemura, S., Saitoh, E., Sanada, K., Isemura, M. and Ito, S. 1986. in Cysteine proteinases and their inhibitors(Turk, V., ed.) pp. 497–505, Walter de Gruyter, Berlin.

Izquierdo-Pulido, M. L., Haard, T. A., Hung, J., and Haard, N. F. 1994. Oryzacystatin and other proteinase inhibitors in rice grain: Potential use as a fish processing aid. J. Agric. Food. Chem. 42: 616–622.

Koide, Y. and Noso, T. 1994. The complete amino acid sequence of pituitary cystatin from chum salmon, Biosci. Biotech. Biochem., 58(1), 164–169.

Lanier, T. C., Hart, K., and Martin, R. E. (Eds.). 1991. A Manual of Standard Methods for Measuring and Specifying the Properties of Surimi. University of North Carolina Sea Grant College Program. Raleigh, N.C.

Lanier, T. C. 1992. Measurement of surimi composition and functional properties. In *Surimi Technology*. T. C. Lanier, and C. M. Lee (Eds.). pp. 123–163. Marcel Dekker, Inc. New York, N.Y.

Liang, Q. and Richardson, T. 1993. Expression and characterization of human lactoferrin in yeast (*Saccharomyces cerevisiae*). J. Agric. Food. Chem. 41: 1800–1807.

Machleidt, W., Assfalg-Machleidt, I. and Auerswald, E. A. 1993. Kinetics and molecular mechanisms of inhibition of cysteine proteinases by their protein inhibitors, in Innovations in Proteinases and Their Inhibitors, Walter de Gruyter & Co., Berlin.

Morrissey, M. T., Wu, J. W., Lin, D. D. and An, H. 1993. Effect of food grade protease inhibitors on autolysis and gel strength of surimi. J. Food Sci. 58:1050–1054.

Okitani, A., Matsukura, U., Kato, H., and Fujimaki, M. 1980. Purification and some properties of a myofibrillar protein-degrading protease, cathepsin L, from rabbit skeletal muscle. J. Biochem. 87: 1133–1143.

Porter, R., Koury, B., and Kudo, G. 1993. Inhibition of protease activity in muscle extracts and surimi from Pacific whiting, *Merluccius productus*, and arrowtooth flounder, *Atheresthes stomias*. Marine Fish. Rev. 55(3): 10–15.

Reppond, K. D. and Babbitt, J. K. 1993. Protease inhibitors affect physical properties of arrowtooth flounder and walleye pollock surimi. *J. Food Sci.* 58: 96–98.

Ritonja, A., Machleidt, W. and Barrett, A. J. 1985. Amino acid sequence of the intracellular cysteine proteinase inhibitor cystatin B from human liver. Biochem. Biophys. Res. Commun. 131:1187–1192.

Saiki, R. K., Gelfand, D. H., Stoffel, S., Scharf, S. J., Higuchi, R., Horn, G. T., Mullis, K. B., Erlich, H. A. 1988. Primer-directed enzymatic amplification of DNA with a thermostable DNA Polymerase. Science 239:487–491.

Sambrook, J., Fritsch, E. F. and Maniatis, T. 1989. Molecular cloning: A Laboratory manual. Cold Spring Harbor Laboratory, Cold Spring Harbor, N.Y.

Seymour, T. A., Morrissey, M. T., Peters, M. Y., and An, H. 1994. Purification and characterization of Pacific whiting proteases. J. Agric. Food Chem. 42(11): 2421–2427.

Seymour, T. A., Morrissey, M. T., Peters, M. Y. and An, H. 1994. Purification and characterization of Pacific whiting proteases. J. Agric. Food Chem. 42 (11): 2421–2427.

Smith, R. A., Duncan, M. J. and Moir, D. T., 1985. Heterologous protein secretion from yeast. Science 229:1219–1224.

Solem, M. L., Rawson, C., Lindburg, K. and Barnes, D. W. 1990. Transforming growth factor b regulates cystatin C in Serum-Free mouse embryo (SFME) cells. Biochem. Biophys. Res. Communication 172: 945–951.

Takio, K., Kominami, E., Bando, Y., Katinuma, N. and Titani, K. 1984. Amino acid sequence of rat epidermal thiol proteinase inhibitor. Biochem. Biophys. Res. Commun. 121:149–154.

Takio, K., Kominami, E., Wakamatsu, N., Katunuma, N. and Titani, K. 1983. Amino acid sequence of rat liver thiol proteinase inhibitor. Biochem. Biophys. Res. Commun. 115:902–908.

Yamamoto, A. 1975. Proteolytic enzymes. Chap. 7, In "Enzymes in Food Processing", 2nd Ed., G. Reed (Ed.). Academic Press, New York.

Yamashita, M. and Konagaya, S. 1990. High activities of cathepsins B, D, H and L in the white muscle of chum salmon in spawning migration. Comp Biochem. Physiol. 95B(1): 149–152.

We claim:

1. An isolated nucleic acid molecule encoding a cystatin protein, wherein the nucleic acid molecule is selected from the group consisting of:

(a) nucleic acid molecules encoding an amino acid sequence as shown in Seq. I.D. No. 2, and (b) nucleic acid molecules capable of hybridizing to a molecule according to (a) under wash conditions of 0.3×SSC at a temperature of 59.4–64.4° C.

2. An isolated nucleic acid molecule according to claim 1 wherein the nucleic acid molecule is capable of hybridizing to the specified molecule under hybridization wash conditions of 0.3×SSC at a temperature of 65.4–98.4° C.

3. An isolated nucleic acid molecule including at least 15 consecutive nucleotides of the nucleic acid sequence shown in Seq. I.D. No. 1, or its complementary strand.

4. The nucleic acid molecule of claim 3 wherein the molecule includes at least 20 consecutive nucleotides of the nucleic acid sequence shown in Seq. I.D. No. 1, or its complementary strand.

5. The nucleic acid molecule of claim 4 wherein the molecule includes the nucleic acid sequence shown as residue numbers 87–416 of Seq. I.D. No. 1.

6. A recombinant vector including the nucleic acid molecule of claim 3.

7. A host cell including the recombinant vector of claim 6.

8. The host cell of claim 7 wherein the host cell is a bacterial host cell.

9. The host cell of claim 7 wherein the host cell is a yeast host cell.

10. An isolated nucleic acid molecule which includes at least 15 consecutive nucleotides of the nucleic acid sequence shown in Seq. I.D. No. 1 and which encodes a fish cystatin.

11. A recombinant vector including the nucleic acid molecule of claim 10.

12. A host cell including the recombinant vector of claim 11.

13. A method of producing cystatin, comprising growing a host cell according to claim 12 in a suitable medium under conditions such that the host cell expresses cystatin and, harvesting said cystatin.

14. The method of claim 13 wherein the host cell is a yeast cell.

15. A purified cystatin protein including at least 7 consecutive amino acids of the sequence shown in Seq. I.D. No. 2.

16. The purified cystatin protein of claim 15 wherein the protein includes at least 10 consecutive amino acids of the sequence shown in Seq. I.D. No. 2.

17. A purified cystatin protein according to claim 16, wherein the protein comprises the amino acid sequence as shown in Seq. I.D. No. 2.

* * * * *

SEQUENCE LISTING

<160> NUMBER OF SEQ ID NOS: 6

<210> SEQ ID NO 1
<211> LENGTH: 674
<212> TYPE: DNA
<213> ORGANISM: Oncorhynchus mykiss
<220> FEATURE:
<221> NAME/KEY: CDS
<222> LOCATION: (21)..(419)

<400> SEQUENCE: 1

```
caaagatatc taacgggaaa atg atc atg gaa tgg aaa atc gtc gtt cct ttg      53
                     Met Ile Met Glu Trp Lys Ile Val Val Pro Leu
                      1               5                  10 ttc gcc gtg gcc ttt acg gtg gcg aac gcc ggt ttg atc gga ggc ccc       101
Phe Ala Val Ala Phe Thr Val Ala Asn Ala Gly Leu Ile Gly Gly Pro
             15                  20                  25 atg gac gca aat atg aac gac caa gga acg aga gac gcc ctg cag ttc       149
Met Asp Ala Asn Met Asn Asp Gln Gly Thr Arg Asp Ala Leu Gln Phe
         30                  35                  40 gcg gtg gtc gaa cac aac aag aaa aca aac gac atg ttt gtc agg cag       197
Ala Val Val Glu His Asn Lys Lys Thr Asn Asp Met Phe Val Arg Gln
     45                  50                  55 gtg gcc aag gtt gtc aat gca cag aag cag gtg gta tct ggg atg aag       245
Val Ala Lys Val Val Asn Ala Gln Lys Gln Val Val Ser Gly Met Lys
 60                  65                  70                  75 tac atc ttc aca gtg cag atg ggc agg acc cca tgc agg aag gga ggt       293
Tyr Ile Phe Thr Val Gln Met Gly Arg Thr Pro Cys Arg Lys Gly Gly
                 80                  85                  90 gtt gag aag gtc tgc tcc gtg cac aag gac cca cag atg gct gtg ccc       341
Val Glu Lys Val Cys Ser Val His Lys Asp Pro Gln Met Ala Val Pro
             95                 100                 105 tac aag tgc acc ttc gag gtg tgg agc cgc ccc tgg atg agc gat atc       389
Tyr Lys Cys Thr Phe Glu Val Trp Ser Arg Pro Trp Met Ser Asp Ile
         110                 115                 120 cag atg gtc aag aac cag tgt gaa agt taa gacccagtga agagaacttc         439
Gln Met Val Lys Asn Gln Cys Glu Ser
     125                 130 aatcaatgtc tagtctaccc aataactact attatctagt actagtgtta tttgttagtc     499
tcaccaatgc agttcaacct ccttgtctag gatgtattca gagaatccca ctaataaaag     559
atgttcaaac ttattgcatg cccacactaa tataagcact taatgcaaac attgctgtct     619
tgagaatgta gtattaaaat gatgcaacag ttaactaaat aaatgttttg gaaca          674
```

<210> SEQ ID NO 2
<211> LENGTH: 111
<212> TYPE: PRT
<213> ORGANISM: Oncorhynchus mykiss

<400> SEQUENCE: 2

```
Gly Leu Ile Gly Gly Pro Met Asp Ala Asn Met Asn Asp Gln Gly Thr
 1               5                  10                  15

Arg Asp Ala Leu Glu Phe Ala Val Val Glu His Asn Lys Lys Thr Asn
             20                  25                  30

Asp Met Phe Val Arg Gln Val Ala Lys Val Val Asn Ala Gln Lys Gln
         35                  40                  45

Val Val Ser Gly Met Lys Tyr Ile Phe Thr Val Gln Met Gly Arg Thr
     50                  55                  60
```

```
Pro Cys Arg Lys Gly Gly Val Glu Lys Val Cys Ser Val His Lys Asp
65                  70                  75                  80

Pro Gln Met Ala Val Pro Tyr Lys Cys Thr Phe Glu Val Trp Ser Ile
                85                  90                  95

Pro Trp Met Ser Asp Ile Gln Met Val Lys Asn Gln Cys Glu Ser
            100                 105                 110

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence:PCR Primer
<220> FEATURE:
<221> NAME/KEY: modified_base
<222> LOCATION: (18, 24)
<223> OTHER INFORMATION: The letter 'n' in this sequence (positions 18 and
      24) can be either adenine, guanine, cytosine, or
      thymine nucleotides

<400> SEQUENCE: 3
aaygcccara arcaggtngt gtcngg                                      26

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence:PCR Primer
<220> FEATURE:
<221> NAME/KEY: modified_base
<222> LOCATION: (7, 19)
<223> OTHER INFORMATION: The letter 'n' in this sequence (at positons 7 and
      19) can be either adenine, guanine, cytosine, or
      thymine nucleotides.

<400> SEQUENCE: 4
catccanggd atrctccana cyacraa                                     27

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:PCR Primer

<400> SEQUENCE: 5
atgatcatgg aatggaaaat cgtc                                        24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:PCR Primer

<400> SEQUENCE: 6
actttcacac tggttcttga ccat                                        24
```